United States Patent [19]

Monvoisin

[11] 4,097,748
[45] Jun. 27, 1978

[54] X-RAY APPARATUS ESPECIALLY FOR MAMMOGRAPHY

[75] Inventor: Jacques Monvoisin, Paris, France

[73] Assignee: Thomson-CSF, Paris, France

[21] Appl. No.: 784,743

[22] Filed: Apr. 5, 1977

[30] Foreign Application Priority Data

Apr. 9, 1976 France .............................. 76 10567

[51] Int. Cl.² .............................................. G03B 41/16
[52] U.S. Cl. ................................ 250/505; 250/439 R; 250/416 TV; 250/511
[58] Field of Search ............... 250/505, 511, 512, 513, 250/514, 320, 321, 322, 323, 416 TV, 439 R

[56] References Cited

U.S. PATENT DOCUMENTS

| | | | |
|---|---|---|---|
| 3,790,799 | 2/1974 | Stein | 250/416 TV |
| 3,866,047 | 2/1975 | Hounsfield | 250/445 T |

*Primary Examiner*—Craig E. Church
*Attorney, Agent, or Firm*—Edwin E. Greigg

[57] ABSTRACT

An X-ray machine, especially for mammography, includes an X-ray source and a suitable table or support for the object to be examined. The table is transparent to X-rays and holds sheets of X-ray film or the like to record the transmitted radiation. In addition to a fixed diaphragm which defines a substantially pyramidal primary beam, there are provided three sets of beam-defining slits, one behind the fixed diaphragm, one ahead of the object of examination and one just ahead of the recording medium. These three slits are disposed in geometrical similarity, i.e., their free width increases in proportion to their distance from the source. Furthermore, each of these slits is movable in a plane normal to the main axis of the primary beam. The three slits together define a narrow angular portion of the primary beam and their motion is so coordinated that the narrow beam is scanned across the object from one extreme position to the other. The successive slits reduce or eliminate the effects of blurring due to the finiteness of the sources and also pervent scattered radiation from the air or from the object of examination to reach the film.

6 Claims, 4 Drawing Figures

X-RAY APPARATUS ESPECIALLY FOR MAMMOGRAPHY

BACKGROUND OF THE INVENTION

This invention relates to an X-ray apparatus, especially for mammography, i.e., an X-ray apparatus intended to be used for the examination of female breasts in which absorption contrasts are generally low.

Known mammography apparatus generally employs a special X-ray tube adapted for the examination of soft tissue and including a molybdenum anode and filter, such as described in U.S. Pat. No. 3,515,874 to Bens & al. patented June 2, 1972 and assigned to the Assignee. Such known apparatus has a beam localizer attached to the housing of the tube which may at the same time serve to compress the breast to be examined against the surface of the support plate. This plate is made from X-ray transmissive material and below it are disposed in a suitable manner film cassettes which are irradiated over the entire surface at the same time. For a variety of reasons, the picture taken with the known apparatus is often unsuitable for ready interpretation. Among these reasons are the following: The small differences in the absorption factor between soft breast tissue and possible tumors; radiation which is scattered both in the air and in the object of examination; reflections taking place on the surface of diaphragms and on the internal walls of the beam localizer; as well as the so-called geometrical blurring which is due to the finite dimension of the focal spot emitting the X-rays.

OBJECT AND SUMMARY OF THE INVENTION

It is a principal object of the invention to provide an X-ray apparatus especially for mammography which overcomes the above-mentioned disadvantages. This and other objects are attained by the invention, by providing that an X-ray beam is caused to scan the object to be examined in a transverse fashion to thereby expose the X-ray film progressively and eliminating scattered radiation as well as the geometric blurring as nearly as possible.

According to the invention, an X-ray apparatus especially for mammography is provided with an X-ray source or generator and an appropriate receiver which is associated with a support for the object to be examined. The foregoing elements are all attached to a column and the X-ray source has a fixed diaphragm which defines an essentially pyramidal beam of rectangular cross section. A principal characteristic of the invention is that it provides, in addition to the above elements, a device for scanning the object to be examined with a narrow beam of X-rays of elongated cross section which is obtained by means of a cooperating system of three movable slits, the direction of motion being perpendicular to the longitudinal axis of the slits. The three slits move simultaneously and in a geometrically similar manner with respect to the source. The first and second of these slits are located between the X-ray source and the object, one of the slits being in the vicinity of the X-ray source and the other being near the object to be examined. The third slit is located between the object and the image receiver. The invention further provides means for moving all three of these slits in a controlled manner.

The invention will be better understood as well as further objects and advantages thereof become more apparent from the ensuing detailed description of preferred embodiments taken in conjunction with the drawing.

DESCRIPTION OF THE PREFERRED EMBODIMENTS

Figure 1:
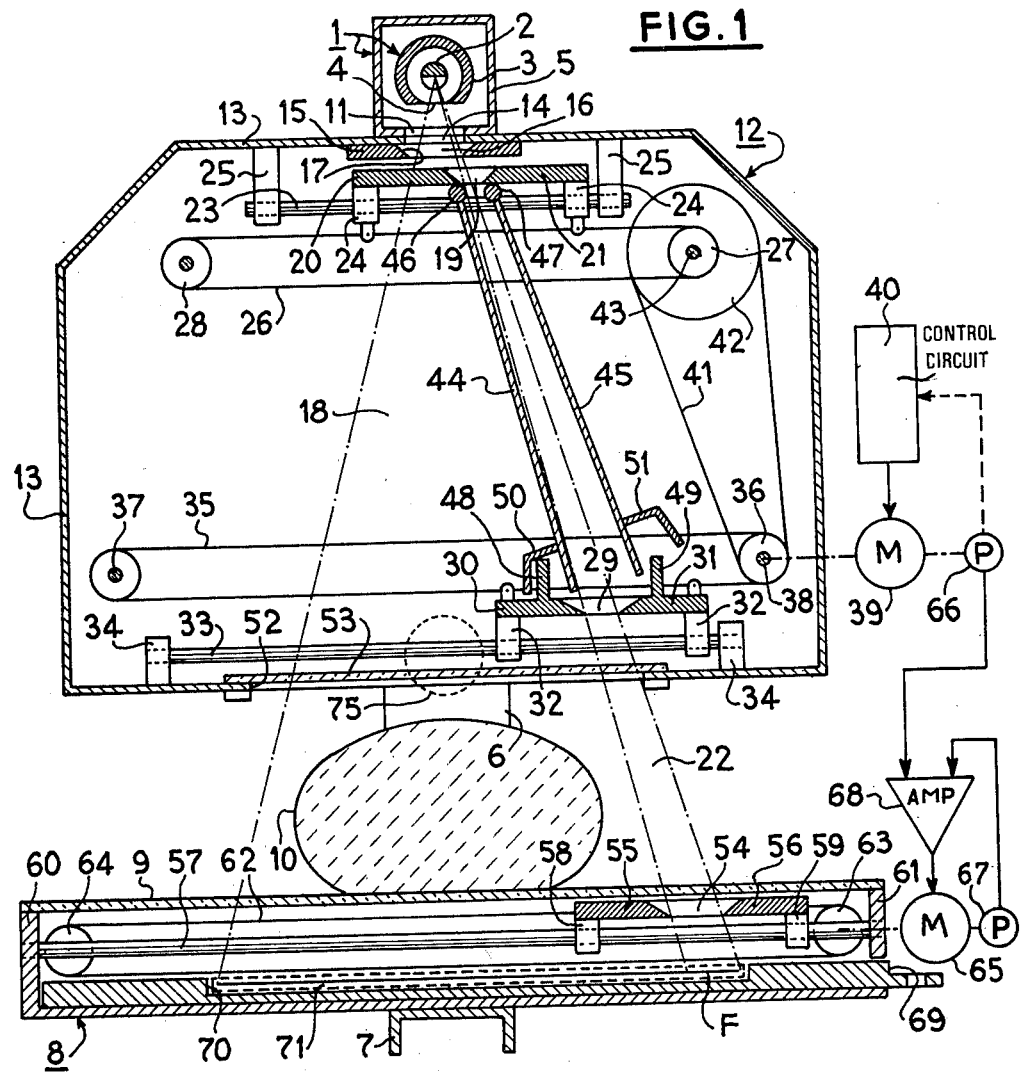
FIG. 1 is a schematic and partially sectional front elevational illustration of an X-ray apparatus according to the invention.

Turning now to FIG. 1, there will be seen an X-ray tube 1 having, for example, a fixed anode 2 constructed from molybdenum and a partially metallic shroud 3 provided with a window 4 and a molybdenum filter such as described for example in the above-cited patent.

Figure 2A:
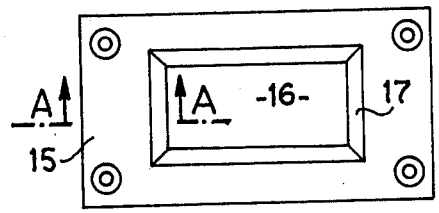
FIG. 2a is a plan view of the fixed diaphragm associated with the X-ray tube.

The X-ray tube 1 is located in a casing 5 which is part of a tube support arm connected to one of the ends of a column 6. The other end of the column 6 has a second arm 7 on which are mounted the film carrier and other associated equipment 8. The upper wall of the film carrier device 8 is a support plate 9 for supporting the object 10 to be examined by radiography and made from a substantially X-ray transparent material. In line with the window 4, the lower wall of the support arme 5 has an opening 11 which permits the X-radiation from the tube 1 to pass in the downward direction. The support arm 5 also carries a housing 12 which represents the support structure for a system of movable slits which constitute a principal feature of the present invention. The metal cover 13 of the housing 12 has an opening 14 in line with the opening 11 of the support arm 5. Defining and surrounding the opening 14 is a diaphragm 15 of fixed size and attached to the cover 13 for defining the total extent of the X-ray beam. This diaphragm 15 is made from a metal plate, for example a steel plate, of sufficient thickness to cause substantial attenuation of the incident X-rays and having a central opening 16 of rectangular shape (see FIG. 2a) which permits an X-ray beam of substantially pyramidal shape to emerge therefrom. As further illustrated in FIGS. 2a and 2b, the interior edges of the diaphragm 15 defining the opening 16 are beveled, i.e., the inside surfaces are inclined at an acute angle with respect to the horizontal plane. This angle is preferably less than 45° so as to prevent any reflected or diffracted radiation from the edges of the opening to return to the center of the beam and thereby deteriorate the contrast by the introduction of parasitic radiation which would be added to the geometric blurring due to the fact that the X-ray source is not a point source.

Experience has shown that a diaphragm 15 made of a steel plate of 4 millimeters thickness and having edges 17 inclined at 15° with respect to the horizontal plane (angle α in FIG. 2b) gives very satisfactory results.

It should be noted here that, inasmuch as this mammography apparatus does not include a radiation localizer to limit the radiation to the breast examined, it may be advantageous to so locate the X-ray tube as to place the focal spot toward the patient relatively to the center of the opening 16 in the diaphragm 15, so as to make the slope of the pyramidal beam nearest the patient as steep as possible to prevent exposing the body of the patient to superfluous amounts of radiation.

Located below the fixed diaphragm 15 and inside of the housing 12 is a first slit 19 formed by two cooperating sides provided by two parallel metal bars 20 and 21. As shown in FIG. 1, this first slit 19 is in one of its extreme positions and is seen to extend in the direction which is perpendicular to the long direction of the opening 16. It thus defines a narrow beam of X-rays 22 having an elongated cross section, i.e., the length of its horizontal cross section is essentially equal to the overall width of the field defined by the fixed diaphragm 15 and its width is only a small fraction of that dimension.

Figure 2B:
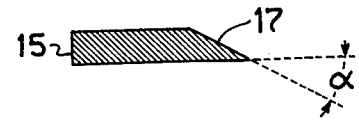
FIG. 2b is a section through the diaphragm along the line A—A.

The adjacent edges of the slit made from the bars 20 and 21 are also beveled or inclined in the manner indicated in FIG. 2b for the same reasons already cited. The width of the first slit 19, i.e., the distance between the beveled edges of the bars 20 and 21 is so chosen as to define a partial exposure on the film plane, the extent of which is, for example, less than a tenth of the available length of the film sheet used. The minimum width of each of the bars 20 and 21 is such that in both of the extreme end positions of the slit 19, only the useful beam 22 illustrated between dash-dotted lines actually reaches the object 10 and the film F and that otherwise the opening 16 in the diaphragm 15 is completely obscured.

The bars 20 and 21 are mounted on dollies 24 which travel on rails 23 that are attached by means of brackets 25 to the housing 12. The lateral movement of the first slit 19 takes place with the aid of two belts or chains 26 which are fixed respectively to the carriages or dollies 24 and are suspended between two pairs of pulleys or pinions 27, 28. The pulleys of each pair are located on both sides of the pyramidal beam 18 and the pairs of pulleys 27, 28 are located respectively on the outside of the extreme positions of the slit 19. One of the pulleys, for example 27, is driven in rotation in a manner yet to be described and the other, for example 28, turns freely on its shaft.

At a shorter distance from the object of examination 10, there is disposed in the apparatus a second movable slit 29 constituted with the aid of two further parallel metal bars 30 and 31, similar to these already described for the slit 19. The bars 30 and 31 are mounted on dollies 32 which can travel along rails 33 attached to the metal wall 13 of the housing 12 by means of supports 34. The carriers 32 or the bars 30, 31 are also affixed to two drive belts 35 suspended on two pairs of pulleys 36 and 37 and located in a manner similar to that described with respect to the first slit 19. The primary object of the second slit 29 is to eliminate the effect of geometrical blurring mentioned above and the width of the bars 30 and 31 is so chosen that in the two extreme positions none of the radiation emanating from the edges of the focal spot through the first slit 19 can actually reach the object 10 or the film F. Thus, the minimum necessary width for the bars 30, 31 increases with the width of the apparent surface of the focal spot.

The shaft 38 on which rotates one of the pairs of pulleys 36, is driven with the aid of an electric motor 39 provided with power by a control circuit 40. A transmission belt or chain 41 couples the motions of the shaft 38 via a reduction pulley 42 to the shaft 43 which carries the pair of pulleys 27 that move the first slit 19. The reduction ratio of the transmission between the shafts 38 and 43 is equal to the ratio of the distance of the first slit 19 from the focal spot to the distance of the second slit 29 from the focal spot of tube 1. In order to insure that the second slit 29 passes only the useful beam 22 previously defined by the first slit 19, the ratio of the widths of these two slits must be equal to the ratio of their respective distances from the focal spot, i.e., they should be geometrically similar with respect to the focal spot.

In a refined version of the present invention, and in order to block extra-focal radiation from the X-ray tube 1 as well as for blocking radiation scattered in the space between the two slits 19 and 29 and to prevent it from reaching the object 10, there are provided two radiation deflectors 44 and 45 located between the bars 20 and 30 as well as between the bars 21 and 31 and surrounding the useful beam 22 and capable of traveling together with the first and second slits. These deflectors 44 and 45 are rectangular or trapezoidal metal plates which pivot about their upper ends at the lower surface of the bars 20 and 21 which constitute the first slit 19 by means of two hinges 46 and 47. To take account of the fact that the distance between the two slits 19 and 29 varies during the motion of the latter, the lower ends of the deflectors 44 and 45 are coupled to the bars 30 and 31 which make up the second slit 29 indirectly by means of extensions 48 and 49 attached respectively to the bars 30 and 31 and by hooks 50 and 51 attached to the deflectors 44 and 45 respectively, which engage the extensions 48 and 49 in the spaces between the hooks and the outside wall of the deflectors. As will be readily appreciated, this disposition permits the deflectors 44 and 45 to retain their position outside of the useful beam 22 during the motion of the slits which takes place simultaneously and in a geometrically similar manner with respect to the source. The bottom of the metal case 13 of the housing 12 which includes the first and second movable slits 19 and 29 has a rectangular opening 52 through which the entire pyramidal beam 18 defined by the fixed diaphragm may pass toward the object to be examined. This opening 52 may be closed by a plate 53 transparent to X-rays.

Located underneath the support table or plate 9 which provides support for the object 10, and which holds a film carrier or a cassette 8, there is located a third movable slit 54 in a position between the object 10 and the film F. It is the purpose of this third slit 54 to prevent radiation scattered within the object 10 from reaching the film. This third slit 54 is also formed by two parallel metal bars 55 and 56 the edges of which are beveled and which are mounted on carriers indicated by dollies 58 and 59 that move on rails 57. The two ends of the rails 57 are fixed within the lateral walls 60 and 61 of the film carrying device 8. Belts 62 suspended around two pairs of pulleys 63, 64 and attached to the carriers 58, 59 permit the geometrically similar displacement of the third slit 54 with respect to the other two slits 19, 29. This displacement is provided for example by means of a second motor 65 powered through a servo circuit having a first potentiometer 66 attached to the shaft of the first motor 39 for indicating the positions of the first two slits 19, 29. There is further provided a second potentiometer 67 attached to the shaft of the second motor 65 to indicate the position of the third slit. An electronic amplifier circuit 68 including a differential amplifier, the inputs of which are attached, respectively, to the taps of the two potentiometers, produces an error signal which is amplified and used to drive the second motor 65. The values and dimensions of the potentiometers 66 and 67 as well as the transmission ratios are calculated so that the movement of the third slit 54 is slaved to be geometrically similar to that of the first two slits in relation to the source of radiation.

It will be noted that the width of the third slit 54 is such as to be geometrically similar to the first and second slits 19, 29 and that the width of the bars 55 and 56 themselves is such as to eliminate the majority of scattered radiation from the object 10.

It should also be noted that the servo mechanism for displacing the third slit 54 could be replaced by a mechanical transmission (not shown) which provides mechanical coupling between the motions of the first motor 39 and one of the pairs of pulleys 63, 64 for example by placing an appropriate transmission in the column 6.

Furthermore, the simultaneous and geometrically similar movement of the three slits 19, 29 and 54 may also be obtained with the aid of a single motor. In that case, the carriers for each of the slits would be connected by a rigid rod that would pivot about an axis passing through the X-ray source 1 and which is perpendicular to the axis of the pyramidal beam 18 as defined by the diaphragm 15. In an improved version of the invention, the control circuit 40 for the drive motor 39 may include means to regulate the speed of displacement such as to be proportional to the sine of the angle which the beam makes with respect to the film plane F. Underneath the third slit 54 and the various guidance and displacement mechanisms, there is located within the film carrier 8 a film cassette drawer 69 which may be pulled from the apparatus and which has a chamber 70 in which may be placed a cassette 71 indicated by dashed lines within which is located the X-ray film F as well as any intensifier screens.

The X-ray film F performs an integration of the total image composed of a succession of partial images which are obtained during the geometrically similar displacements of the three movable slits 19, 29 and 54. This exposure is equivalent to a scanning of the object with a narrow beam of X-rays which produces the advantage of eliminating the geometrical blurring, the extra-focal radiation and any radiation diffused or scattered within the object to be examined and in the surrounding air.

It will be appreciated that, instead of the X-ray cassette 71 and the drawer 69, there may be employed any type of known image receiving means, for example, a film or cassette changer, or of the type including an image intensifier and a television camera. However, if a television display is used, means must be provided for integrating the successive images into a total X-ray picture. Such a purpose may be served by a storage camera tube, a recording storage tube or an image retaining display tube.

Figure 3:
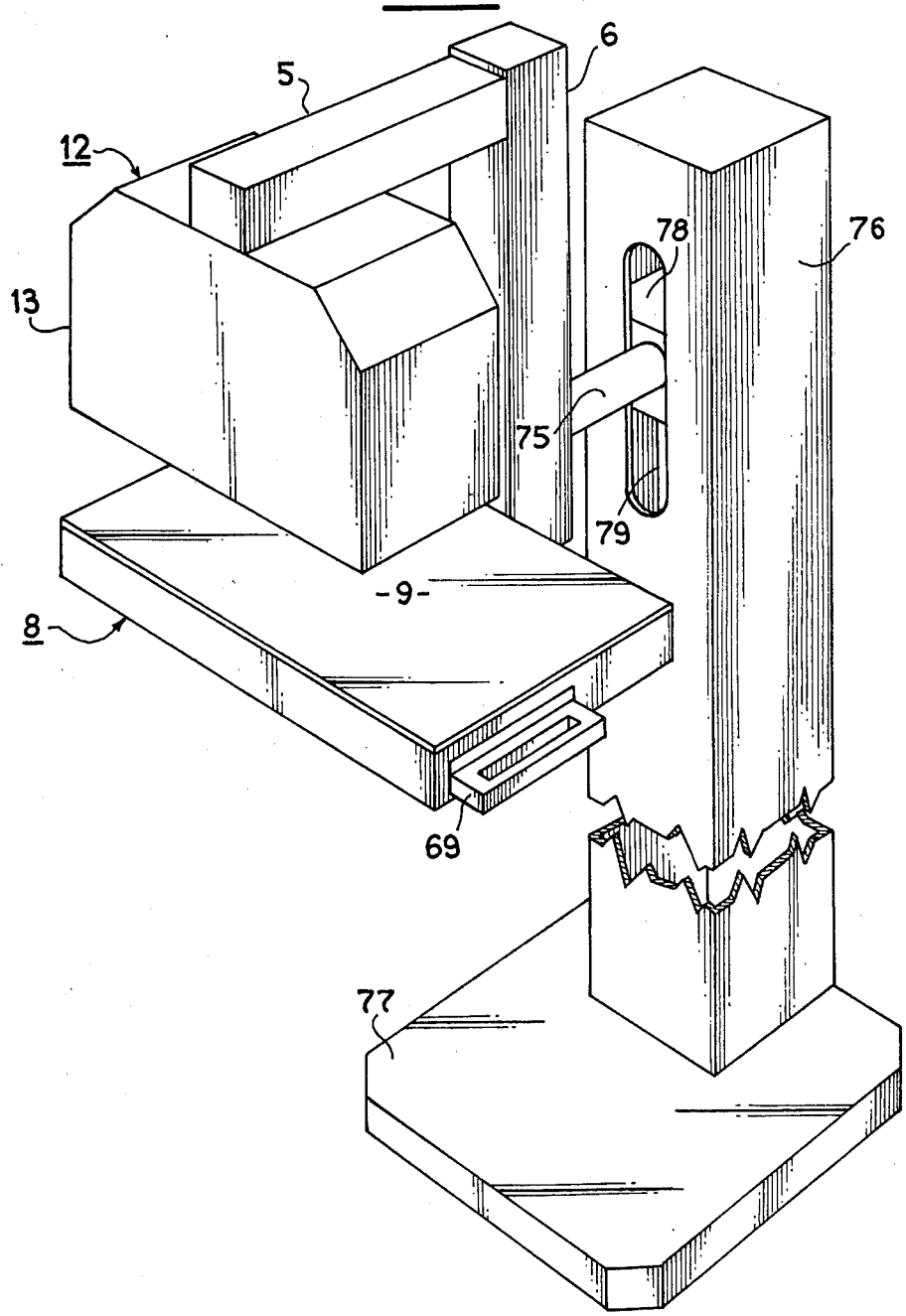
FIG. 3 is a perspective view of the overall X-ray apparatus according to the invention.

FIG. 3 is a perspective illustration of an overall apparatus of the invention for X-ray mammography in which the portions relevant to FIG. 1 are shown to be mounted on a support column.

FIG. 3 shows the tube-carrying arm 5 connected at one of its ends to the column 6 which also carries the cassette carrier 8. The upper end of the arm 5 holds the housing 12 in which are located the two movable slits 19, 29 of FIG. 1 as well as their displacement mechanisms.

The column 6 is itself mounted on a carrier shaft 75 capable of pivoting by plus or minus 90° about its own axis within a support column 76 mounted on a base plate 77.

In an improved version of the invention, the shaft 75 may also be displaced vertically by means of a movable carriage 78 which can travel up or down on rails or the like under the influence of a jack or a known lifting mechanism (not shown). The oblong opening 79 makes possible the vertical motion of the arbor 75 and roughly indicates the limits of its vertical travel.

The X-ray apparatus according to the present invention is principally intended for mammography, i.e., for the X-ray examination of the human breast in order to detect therein the existence of pathological tumors. Its substantial improvement over existing and known mammography apparatus is that it permits obtaining X-ray pictures of substantially improved quality. The improved quality of the pictures obtained with the apparatus of the present invention is due to the elimination of the geometrical blurring, of the diffused and scattered radiation and of radiation from outside the center of the focal spot. This improvement is principally due to the disposition of three slits which move simultaneously and the dimensions of which are geometrically similar and which produce a narrow X-ray beam which is swept, by motion of the slits, over the object to be examined. Two of the slits are located between the X-ray source and the object, one being close to the source and the other close to the object, while the third slit is located between the object and the image receiver, i.e., the X-ray film.

It will be appreciated that the entire system of slits may be rotated by 90° from the direction indicated in FIG. 1, i.e., to scan the beam from the front to the rear of the apparatus or in the reverse direction instead of going from side to side as illustrated and discussed.

The foregoing relates to preferred exemplary embodiments of the invention, it being understood that other variants and embodiments thereof are possible within the spirit and scope of the invention, the latter being defined by the appended claims.

What is claimed is:

1. In an X-ray machine, especially for mammography which includes a source of X-radiation, means for holding said source of X-radiation, for holding an object to be irradiated and for holding means for forming an image from said X-radiation, said source having a fixed diaphragm which defines a beam of X-radiation which has an angular deviation such that its shape resembles a pyramid of rectangular cross section, said X-ray machine further including beam-defining means for passing only a limited portion of said pyramidal beam, said beam-defining means being capable of motion in a plane perpendicular to the axis of said pyramidal beam, the improvement comprising:

said beam-defining means includes in combination:
a first slit disposed near said source for defining a narrow beam the long extent of which is substantially perpendicular to the motion of said beam-defining means;
a second slit disposed near and ahead of said object;
a third slit, disposed near and behind said object and ahead of said image forming means; and
means for displacing said first, second and third slit in unison along mutually parallel planes and in a manner to maintain geometrical similarity, i.e., to maintain a line of sight through said slits to said source of X-radiation.

2. A machine as defined by claim 1, wherein each of said first, second and third slits is defined by a pair of cooperating metal bars with adjacent substantially parallel edges, said edges being beveled to prevent reflected X-rays from entering the useful beam field.

3. An apparatus as defined by claim 1, the improvement further comprising an electric motor for moving said first and second slits and a mechanical transmission for coupling the motions of said first and second slits in a manner which maintains geometric similarity, i.e., a line of sight through said first and second slits to said source and further comprising a second motor for driving said third slit as well as a servo control circuit for moving said third slit in a manner dependent on the motion of said first and second slits and in a manner aligned angularly with the position of said first and second slits.

4. An apparatus as defined by claim 1, wherein each of said first, second and third slits is defined by substantially parallel metal bars, and wherein the width of the bars forming said first slit nearest said fixed diaphragm is such as to obstruct said diaphragm totally in the extreme lateral positions of said first slit and to permit a passage of only a narrow beam in positions in between said extreme positions.

5. A machine as defined by claim 4, wherein the width of the bars defining said second slit is such as to prevent a substantial portion of the geometric blurring due to the finite dimensions of the source of radiation.

6. An apparatus as defined by claim 1, further comprising a pair of radiation reflectors defined by two metal plates suspended to pivot from said bars defining said first slit and coupled to said bars forming said second slit; whereby the lower portion of said reflectors shares the motion of said second slit while permitting the passage of said narrow beam of X-radiation therebetween in all positions of said slits.

* * * * *